United States Patent [19]
Figliola

[11] Patent Number: 4,659,495
[45] Date of Patent: Apr. 21, 1987

[54] BATH PRODUCT AND METHOD FOR TREATING BATH WATER

[76] Inventor: Vincent N. Figliola, 7265 Village Dr., Las Cruces, N. Mex. 88001

[21] Appl. No.: 761,985

[22] Filed: Aug. 2, 1985

Related U.S. Application Data

[63] Continuation-in-part of Ser. No. 486,724, Apr. 20, 1983, abandoned.

[51] Int. Cl.[4] .............................................. C11D 17/00
[52] U.S. Cl. ......................................... 252/90; 252/92; 252/174; 206/0.5; 206/77.1
[58] Field of Search .................. 206/0.5, 77.1; 252/90, 252/134, 174, 92, 93; 424/18

[56] References Cited

U.S. PATENT DOCUMENTS

| | | | |
|---|---|---|---|
| 1,619,105 | 3/1927 | Eggan | 401/196 |
| 2,149,713 | 3/1939 | Webber | 206/0.5 |
| 2,470,851 | 5/1949 | Hermanson | 252/93 |
| 2,539,395 | 1/1951 | Banks | 252/93 |
| 2,636,008 | 4/1953 | Jurgensen et al. | 252/93 |
| 2,852,795 | 9/1958 | Hermanson et al. | 15/131.1 |
| 3,150,049 | 9/1964 | Emory | 167/90 |
| 3,237,550 | 3/1966 | Christopher | 99/287 |
| 3,294,224 | 12/1966 | Horwitz | 206/46 |
| 3,436,345 | 4/1969 | Goodenough et al. | 210/62 |
| 4,188,304 | 2/1980 | Clarke et al. | 252/93 |

FOREIGN PATENT DOCUMENTS

WO80/01077  5/1980  World Int. Prop. O.

Primary Examiner—Paul Lieberman
Assistant Examiner—Hoa Van Le
Attorney, Agent, or Firm—Pennie & Edmonds

[57] ABSTRACT

A bath product and a method for conditioning bath water and bather's skin. The bath product comprises a water permeable bag, and a water soluble powder located within the bag for conditioning a supply of bath water and the bather's skin. The product further comprises a handle to facilitate holding the bag in the bath water, and a connecting device connecting the handle to the bag.

9 Claims, 6 Drawing Figures 4,659,495

BATH PRODUCT AND METHOD FOR TREATING BATH WATER

BACKGROUND OF THE INVENTION

This is a continuation-in-part of application Ser. No. 486,724 filed Apr. 20, 1983, now abandoned.

FIELD OF THE INVENTION

This invention generally relates to bath products and to methods of conditioning bath water and a bather's skin, and more particularly to a product and a method that may be easily employed to leave the skin of a bather moisturized and delicately scented, and that also helps to create a relaxing and comforting aura.

DESCRIPTION OF RELATED ART INCLUDING INFORMATION DISCLOSED PURSUANT TO 37 C.F.R. §§1.97-1.99

Prior art bath water treatment products and methods are believed to suffer from one or more of several disadvantages. For example, most powder mixes which are added to the bath water do not completely dissolve in the water, and some of the powder settles undissolved on the bottom of the bathtub. The undissolved powder particles may make sitting in the bathtub very uncomfortable. This is directly contrary to the primary purpose of using the bath additive, which is to produce a relaxing and comforting feeling.

Also, most liquid bath additives do not thoroughly mix with the bath water, accumulating instead on the surface of the water. This uneven distribution of the additive in the water results in an uneven distribution of the effects of the additive on the body of the bather, with the portion of the body that is below the top surface of the water receiving very little, if any, benefit from the additive. The accumulation of the liquid additive on the surface of the water also may result in an oily ring on the sides of the bathtub, and cleaning this ring off the side of the bathtub after the bath is completed can destroy the ambience the bath was taken to create.

Moreover, with both liquid and powder prior art bath products, it is difficult for the bather to determine and use the right amount of the product. If too little of the product is used, the bather does not fully obtain the advantages which may be achieved from the additive. On the other hand, using too much of the product is not only cost inefficient, but also may actually adversely affect the bather's efforts to create a relaxing and soothing atmosphere because the excess additive may add to the oily ring on the sides of the bathtub if the additive is a liquid, or accumulate undissolved on the bottom of the bathtub if the additive is a powder. In addition, often a person must use several separate products to condition bath water in a desired manner. That is, often a first product, for instance a skin moisturizer, is added to the bath water, then a second product, for example, fragrances, are added. This is a relatively complex and clumsy process.

SUMMARY OF THE INVENTION

In view of the above, an object of the present invention is to help create an aura of body comfort with a scented, premeasured, moisturizing and muscle soothing bath product.

Another object of this invention is to condition bath water with an additive which does not collect on the top or settle to the bottom of the bath water.

A further object of the present invention is to condition bath water and the bather's skin with a premeasured supply of water soluble powder particles, including one, several, or all of the following ingredients: ground herbs, fragrant agents, moisturizing beads, and coloring agents, and where individual powder particles are held within a water permeable bag until dissolved.

These and other objects are attained with a bath product comprising a water permeable bag and a water soluble powder located within the bag for conditioning a supply of bath water. The product further comprises a handle to facilitate holding the bag in the bath water, and connecting means connecting the handle to the bag.

DETAILED DESCRIPTION OF THE PREFERRED EMBODIMENT

Bath Product

Figure 1:
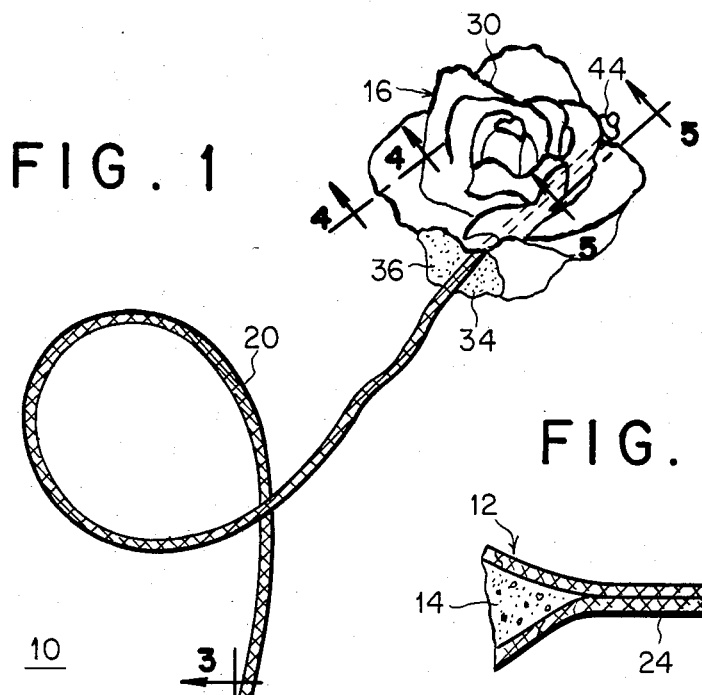
FIG. 1 is a front view showing a bath product in accordance with a preferred embodiment of the present invention.

FIG. 1 illustrates bath product 10 in accordance with a preferred embodiment of the present invention, and generally the product comprises bag 12, powder 14, handle 16, and connecting means 20. Bag 12 is water permeable; that is, the bag defines a multitude of pores which allow water to flow into and through the bag. At the same time, though, bag 12 has sufficient wet strength to maintain its integrity when soaked in water. Bag 12 may be formed, for example, from the same material from which conventional tea bags are formed.

Powder 14 is water soluble and is located within bag 12 for conditioning a supply of bath water in a manner more fully explained below. Powder 14 is comprised of a premeasured supply of powder particles including at least one, and preferably more or all, of the following ingredients: ground herbs, fragrant agents, moisturizing beads, and coloring agents. The herbs improve the medicinal effects of the bath water. The fragrant agents, which may be synthetically made, impart a fragrance to the bath water and to the bather. The moisturizing beads, when dissolved in the bath water, help to moisturize the bather's skin.

By moisturizing beads is meant capsules, prills, and molded or free flowing powders made from materials which occlude, entrap, absorb or adsorb moisturizing agents, i.e., agents which form a thin film on the skin surface making it feel smooth and/or delaying to some degree the evaporation of water. These moisturizing agents have been known and referred to in the art as emollients. For purposes of this invention reference to dissolving the moisturizing beads means dissolving the beads and the included moisturizing agents or simply dissolving or uniformly dispersing the moisturizing agents.

The emollient or moisturizing oils which can be utilized in or to form moisturizing beads and generally known and referred to in the art as bath oils. Suitable bath or emollient oils include, for example, mink oil, lanolin, liquid lanolin esters and other lanolin derivaties, cocoa butter, lower alkanol esters of saturated fatty acids such as isopropyl palmitate, ispropyl myristate, isopropyl stearate, isopropyl linoleate, methyl laurate, ethyl stearate, and the like. Also suitable are the glycerol esters of saturated fatty acids, e.g., glyceryl monostearate, glyceryl monolaurate, glyceryl tripalmitate, the cholesterol esters of saturated fatty acids, polyethers such as polymers of propylene oxide, $C_{12-18}$ alcohols, e.g., oleyl alcohol, cetyl alcohol, stearyl alcohol, lauryl alcohol, and adducts of $C_{12-18}$ alcohols with 1 to 4 moles of ethylene oxide, e.g., ethoxylated lauryl alcohol containing about 1 mole of ethylene oxide per mole of lauryl alcohol, glycols such as dipropylene glycol, oily liquids, e.g., the vegetable oils such as olive oil, cottonseed oil, corn oil, almond oil, peanut oil, and the like, hydrocarbons such as mineral oils, light liquid petrolatum and the like, and similar absorbable substances which soften, moisturize or give the effect of softening or moisturizing the skin.

The emollient or moisture oils may be used in the moisture beads of the instant invention by art recognized techniques such as occluding or complexing them with solid compounds such as ureas or thioureas to give molded, prilled, crystalline or free flowing powders, mixing them with oatmeal or encapsulating them with any of the materals which are soluble, and preferably slowly soluble, in water such as gelatin, polyvinyl alcohol, polyvinyl acetate, carboxymethylcellulose and hydroxyethycellulose. Different times for release of the encapsulated materials may be achieved by the use of encapsulated materials having different thickness or for example, by varying the "bloom" of the gelatin.

Any of the standard moisturizing bead compositions can be used to give the sought results of this invention. Commercial examples include Jean Nate Very Silky Moisturizing Bath Beads from CHARLES OF THE RITZ GROUP LTD., CALGON Bath Oil Beads from Beecham Products, VASELINE Brand Intensive Care Bath Beads and Vaseline Intensive Care Mineral Baths from Chesebrough-Pond's Inc., or POND'S Cream & Cocoa Butter TROPICAL BATH BEADS.

The coloring agents provide a pleasing color to the bath water, and can be suggestive of the fragrant agent used. For example, a coloring agent which imparts a pink color to the water can be used in conjunction with a rose fragrant agent. Similarly, a blue agent can be used to suggest hyacinth, and a green agent for mimosa.

Figure 2:
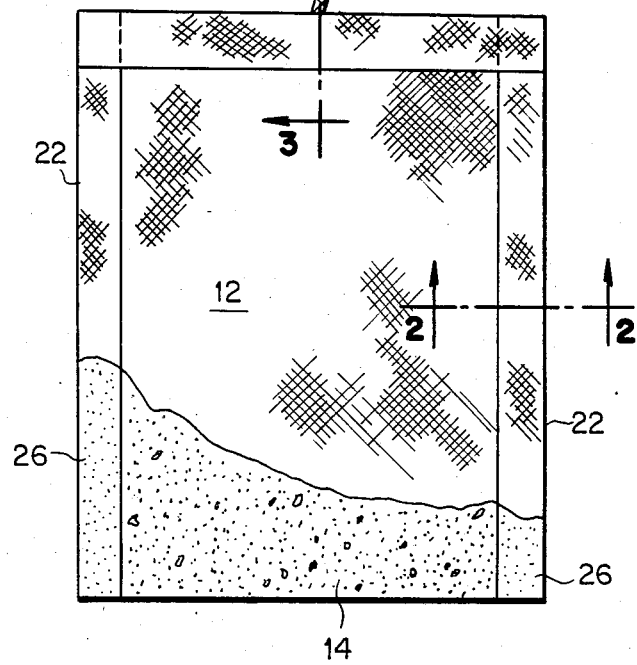
FIGS. 2 and 3 are a cross sectional views of portions of the bag shown in FIG. 1, taken along lines II—II and III—III thereof respectively.

Bag 12 may be made by simply placing a premeasured supply of powder 14 on a flat, precut sheet of material, and folding this material to form a closed bag. It may be noted that the size of bag 12 and the specific amount of powder 14 in the bag may be varied depending on the quantity of water or the size of the tub with which product 10 is intended to be used. For instance, a larger bag 12 and powder supply 14 than what is represented in the drawings may be employed if product 10 is intended for use with a hot tub. Preferably, as shown in FIG. 2, contiguous peripheral edges 22 and 24 of the sheet forming bag 12 are secured together along their entire common length by water insoluble means 26 such as a water insoluble glue. This arrangement is of utility because with it, the peripheral edges of bag 12 are held closed when the bag is immersed in water, preventing undissolved powder particles 14 from passing from the bag through the peripheral edges thereof.

Handle 16 is provided to facilitate holding bag 12 in the bath water. Preferably, handle 16 includes indicia 30 such as a decorative shape or design indicating the fragrance of the powder in bag 12. For example, handle 16 may be in the shape of a rose, hyacinth or mimosa. With the embodiment of bath product 10 illustrated in the drawings, with particular reference to FIGS. 4 and 5, handle 16 is comprised of substantially identical front and back faces 32 and 34, and adhesive means 36 securing together these faces.

Referring back to FIG. 1, connecting means 20 connects handle 16 to bag 12, and preferably the connecting means simply is a length of string secured to both the handle and the bag. It should be pointed out, however, that other types of connecting means 20 may be utilized in the practice of the present invention. For example, a chain, band, or cloth strip may be used to connect handle 16 to bag 12. Furthermore, connecting means 20 may be secured to handle 16 and to bag 12 in various ways, for instance by being taped, glued, or stapled to the handle and the bag.

Figure 3:
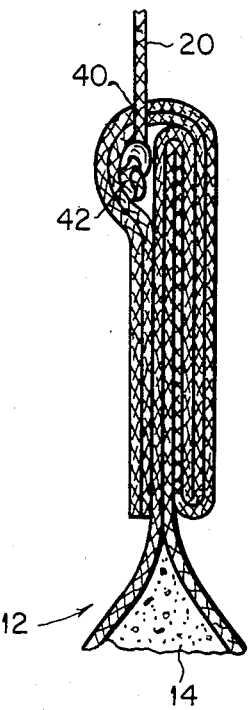

Preferably, with reference to FIG. 3, a top portion of bag 12 defines string opening 40 and a first, or lower, portion of string 20 extends through the string opening and includes knot 42 which is located below the surfaces of the bag defining the string opening and which is larger than the string opening to inhibit the first portion of the string from passing, or being pulled, upward through opening 40.

Figure 4:
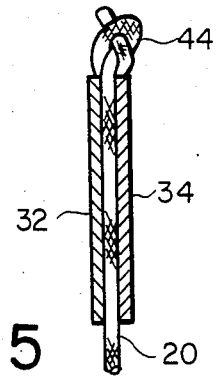
FIGS. 4 and 5 are cross-sectional views of portions of the handle shown in FIG. 1, taken along lines IV—IV and V—V thereof respectively.
Figure 5:
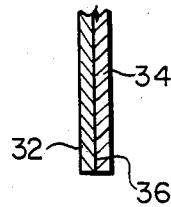

At the same time, now referring to FIG. 4, preferably string 20 extends and is securely compressed between the opposed faces 32 and 34 of handle 16. With this structural relationship, string 20 does not obstruct any design on the outside of handle 16, and in fact may be used to contribute to the impression created by that design, for instance by suggesting a flower stem. To further secure string 20 to handle 16, a second, or upper, portion of the string may extend above the handle and include knot 44 which inhibits the string from sliding, or being pulled, downward between handle faces 32 and 34.

Method For Conditioning Bath Water and Skin

Figure 6:
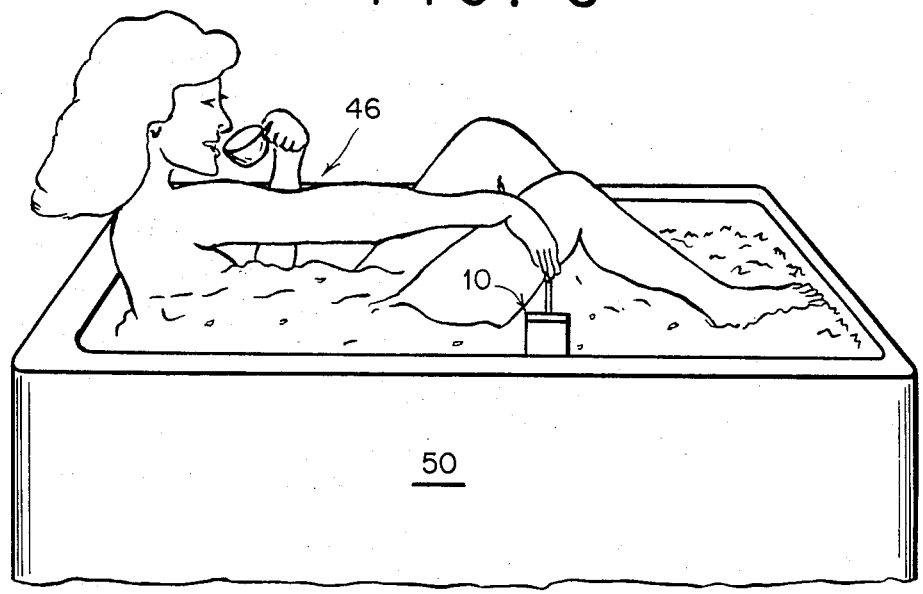
FIG. 6 is a simplified pictorial view showing the manner in which the bath product shown in FIG. 1 may be employed to condition bath water and the bather's skin.

To use bath product 10, with reference to FIG. 6 which pictorially shows bather 46 taking a bath in bathtub 50, the bather simply holds bag 12 in the bath water. Water flows into and through bag 12, dissolving powder 14 within the bag and carrying the dissolved powder out of the bag, where the dissolved powder mixes with and conditions the rest of the bath water. Bag 12 may be held in the bath water until substantially all powder particles 14 are dissolved, which preferably occurs between 20 seconds and three minutes, after which the bag may be discarded. It should be noted that, while bag 12 is in the water, individual powder particles 14 are maintained in the bag since the size of these particles is larger than the size of the pores defined by the bag and since the peripheral edges of the bag are maintained closed by securing means 26. By keeping undissolved powder 14 in bag 12, no powder accumulates or settles on the bottom of the bathtub 50.

In order to facilitate a free flow of water through bag 12, preferably the bag is kept away from the body of bather 46, and in particular the bag is held via handle 20, which is spaced from the bag. Also, to promote a quick and uniform conditioning of the bath water by dissolved particles 14 from bag 12, the bag may be held in the bath water spaced from the bottom and sides of bathtub 50. The length of string 20 between bag 12 and handle 16 preferably is between 8 and 8½ inches. This specific length of string 20 discourages bather 46 from hanging bag 12 over the side of bathtub 50, while still providing the bather with a sufficient length of string to immerse the bag completely in the bath water. This particular string length also allows bather 46 to move bag 12 liberally up, down, and around in the bath water, further promoting a uniform conditioning of that water, while keeping the bather's hands dry.

As will be appreciated from the above remarks, bath product 10 may be employed to condition a supply of bath water in a very simple, elegant and quick, yet effective manner. Because the quantity of powder is premeasured, the bather need not become concerned with attempting to determine the proper amount of powder to use; and since bag 12 may be provided with several or all of the bath additive ingredients, the bather does not have to keep or use a plurality of separate products and containers. Moreover, the specific arrangement described above is especially well suited for thoroughly and uniformly conditioning the bath water without undissolved powder particles collecting on the bottom of the bathtub and without any oily ring developing on the top of the bathwater. The end result is a very relaxed, carefree arrangement for conditioning the bath water and the bather's skin which itself significantly contributes to the development of a soothing, comforting, and sensual atmosphere.

While it is apparent that the invention herein disclosed is well calculated to fulfill the objects stated above, it will be appreciated that numerous modifications and embodiments may be devised by those skilled in the art, and it is intended that the appended claims cover all such modifications and embodiments as fall within the true spirit and scope of the present invention.

What is claimed is:

1. A bath water and skin conditioning product comprising:
   (a) a water permeable bag;
   (b) a water soluble, water conditioning powder located within the bag for conditioning a supply of bath water and the skin of a bather, the powder consisting essentially of moisturizing beads;
   (c) a handle to facilitate holding and moving the bag in the bath water; and
   (d) connecting means connecting the handle to the bag, wherein the bag allows water to pass into and through the bag to dissolve the powder therein, said dissolution being capable of being controlled and facilitated by manipulation of said handle and bag.

2. A bath product according to claim 1 wherein the bag includes:
   (a) a sheet of folded material having contiguous, peripheral edges; and
   (b) water insoluble means securing together the contiguous, peripheral edges of the sheet to maintain the peripheral edge of the bag closed when the bag is immersed in the bath water.

3. A bath product according to claim 1 wherein:
   (a) the handle includes a front face, a back face, and adhesive means securing together the front and back faces; and
   (b) the connecting means includes a string compressed between the front and back faces of the handle to secure the string thereto.

4. A bath product according to claim 3 wherein the length of the string between the bag and the handle is between 8 and 8½ inches.

5. A bath product comprising:
   (a) a bag defining a string opening and a multitude of pores to allow water to pass into and through the bag;
   (b) a water soluble powder consisting essentially of moisturizing beads located within the bag to condition a supply of bath water and the skin of a bather and including a multitude of particles larger than the pores defined by the bag, wherein the bag inhibits movement of undissolved powder particles outward through the bag;
   (c) a handle spaced from the bag to facilitate holding and moving the bag in the bath water, and including a front face, a back face, and adhesive means securing together the front and back faces; and
   (d) a string connecting the handle to the bag and including:
      (i) a first portion extending through the string opening defined by the bag and having a first knot located below the surfaces of the bag defining the string opening to inhibit upward movement of the first portion of the string through the string opening, and
      (ii) a second portion extending through the handle, between bottom and top sections of the perimeter thereof, compressed between the front and back faces of the handle, and having a second knot located above the handle to inhibit downward movement of the second portion of the string through the handle.

6. A method of treating bath water comprising:
   (a) holding a water permeable bag having a premeasured amount of water soluble powder particles consisting essentially of moisturizing beads in the bath water until substantially all the powder particles are dissolved; and
   (b) maintaining each individual powder particle in the bag until the particle dissolves.

7. A method according to claim 6 wherein the bath water is located within a bathtub having a bottom and a plurality of sides, and the holding step includes the step of keeping the bag spaced from the bottom and the sides of the bathtub.

8. A method according to claim 7 wherein the holding step further includes the step of holding the bag via a handle to facilitate the flow of bath water through the bag.

9. A method according to claim 8 wherein the holding step further includes the step of holding the bag in the bath water between twenty seconds and 3 minutes.

* * * * *